(12) United States Patent
Steger

(10) Patent No.: US 6,889,556 B2
(45) Date of Patent: May 10, 2005

(54) PRESSURE SENSOR

(75) Inventor: Juergen Steger, Koerle (DE)

(73) Assignee: B. Braun Melsungen AG, Melsungen (DE)

( * ) Notice: Subject to any disclaimer, the term of this patent is extended or adjusted under 35 U.S.C. 154(b) by 176 days.

(21) Appl. No.: 10/421,145

(22) Filed: Apr. 23, 2003

(65) Prior Publication Data
US 2003/0217602 A1 Nov. 27, 2003

(30) Foreign Application Priority Data
Apr. 24, 2002 (DE) .......................... 202 06 474

(51) Int. Cl.⁷ .................................................. G01L 7/00
(52) U.S. Cl. .......................................... 73/756; 73/824
(58) Field of Search .......................... 73/700, 715, 730, 73/756, 818, 824, 861.355–861.357

(56) References Cited

U.S. PATENT DOCUMENTS 2,783,325 A * 2/1957 Luckey ..................... 200/83 R
4,250,434 A * 2/1981 Valansot .................... 315/362
5,610,342 A * 3/1997 Wenger et al. .......... 73/861.354
6,047,457 A * 4/2000 Bitto et al. ............. 73/861.355
6,575,040 B2 * 6/2003 Dietrich ....................... 73/756
6,799,643 B2 * 10/2004 Voulkidis et al. ............ 173/170

* cited by examiner

Primary Examiner—Edward Lefkowitz
Assistant Examiner—Alandra Ellington
(74) Attorney, Agent, or Firm—Osha & May LLP; John W. Montgomery

(57) ABSTRACT

A pressure sensor is provided with two supporting bodies (10,11) with plane supporting surfaces (12,13) between which a hose (14) is compressed or flattened. For measuring the internal pressure of the hose (14), pressure transmission means (17 or 22) is displaceable in a gap (16) that is arranged at a supporting body (10 or 11) adjacent to the compressed of flattened hose (14). The pressure transmission means (17 or 22) presses against the plane surface of the flattened-hose (14) and is supported on a force sensor (19). Thus, the deformation forces generated upon compressing the hose are eliminated for the measurement of pressure.

14 Claims, 1 Drawing Sheet

PRESSURE SENSOR

RELATED APPLICATIONS

This application claims priority from Germany Patent Application No. 202 06 474.3 filed on Apr. 24, 2002, the disclosure of which is incorporated herein by reference.

FIELD OF THE INVENTION

The invention relates to a pressure sensor comprising a hose for passing a fluid, two supporting bodies deforming the cross-section of the hose and a force sensor reacting to the internal pressure of the hose.

BACKGROUND

In medical technics, hoses are used to supply liquid to a patient by infusion or to take liquid from a patient or to convey liquid between apparatuses or machines. In doing so, it is necessary to detect a hose occlusion such as it occurs, for example, if the hose is kinked. Further, it is often necessary to limit the internal pressure of a hose.

From DE 40 13 403 C2, a pressure sensor is known where the hose is compressed between two supporting bodies. The one supporting body forms a stationary abutment and the other supporting body is movable and supported by a force sensor. The force sensor detects the force acting upon the hose. This force is counteracted by the restoring force of the hose and the internal pressure of the hose. To measure the internal pressure with sufficient precision, the utilized hose and its restoring ability have to be known. For detecting the material properties of the hose, a time-consuming comparison measurement is performed. As a rule, however, the material properties of the hose depend on the temperature so that different comparison measurements would have to be conducted at different operational temperatures. The deformation force required for deforming the hose, which is particularly high in the border zones of the hose, superimposes the pressure signal up to the factor 10. Therefore, combined measurements of both forces are very incorrect. Moreover, the deformation force is not constant in time over the period of service of the hose.

A similar pressure sensor where a measurement of the hose properties is made first before the signals of the force sensor are evaluated is described in DE 38 38 689 C1. Here, the restoring forces of the hose are also superimposed by the force generated by the internal hose pressure.

There is a need for a pressure sensor the measuring signals of which are largely independent of the utilized hose and the placement duration thereof. This and other needs are addressed, according to aspects of the invention, with the features set forth herein.

BRIEF DESCRIPTION OF THE DRAWINGS

Hereinafter, embodiments of the invention will be explained in detail with reference to the drawings.

DETAILED DESCRIPTION OF A PREFERRED EMBODIMENT

Figure 1:
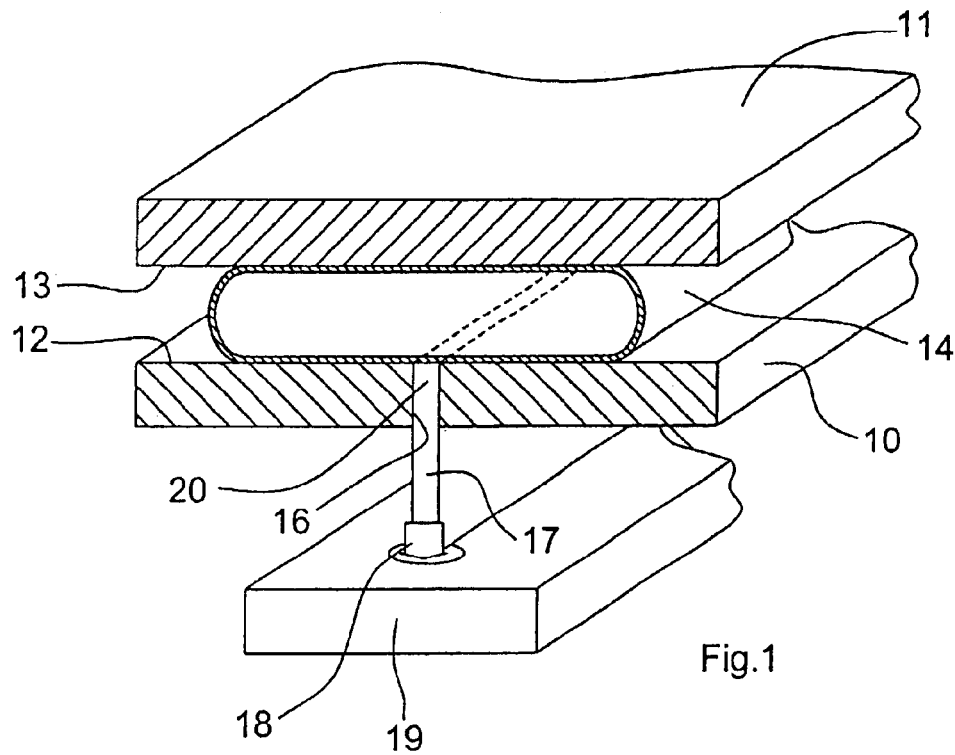
FIG. 1 shows a schematic perspective sectional view of a first embodiment of a pressure sensor with a solid web.

The pressure sensor according to FIG. 1 comprises two plate-shaped supporting bodies 10 and 11, each having a plane supporting surface 12 and 13, respectively. Between the parallel supporting surfaces 12 and 13, a hose 14 is flattened. To this end, the supporting bodies 10 and 11 are relatively movable toward each other. One of the supporting bodies 10 or 11 may be movable towards the other supporting body.

The hose 14 comprises of a flexible material that is elastic and thus has a restoring ability. In the uncompressed state, the cross-section of the hose 14 is round. In the flattened state of the hose, the hose cross-section has a longitudinal shape as illustrated in FIG. 1. In the hose lumen 15, there is a liquid, for example an infusion solution, which is supplied to a patent.

Through the supporting body 10, a longitudinally extending gap 16 extends which is arranged in the central portion of the flattened hose 14. The hose 14 is held in a defined position between the supporting bodies 10,11 by (non-illustrated) side walls. The gap 16 extends through the thickness of the supporting body 10. In the gap 16, a force transmission means in the form of a web 17 is arranged. The web 17 is displaceable transversely to the supporting body 10. It extends in longitudinal direction of the hose 14. At the one end of the web 17, a foot 18 is provided which presses against a force sensor 19. The force sensor 19 is rigidly mounted to the supporting body 10 by (non-illustrated) locking means. The force sensor 19, for example, comprises expansion measuring strips that are connected to form a bridge circuit and generate an electrical signal that is proportional to the force F acting upon the force sensor 19.

Accordingly, at least one of the supporting bodies includes a force transmission means that is movable relative to this supporting body and presses against the hose with one end and against the force sensor with the other end.

The force transmission means should be spaced from the two bending portions of the hose as far as possible. Particularly, it has a width that amounts to maximally 25% of the lumen (width) of the hose deformed by the supporting bodies, and particularly maximally 15%.

Thereby, it is achieved that the deformation forces of the hose are received by the supporting bodies and substantially kept away from the force sensor. The force sensor is decoupled from the supporting bodies, i.e., it does not react to forces generated by loading the supporting bodies. Particularly, the supporting bodies provide for the support in the two curved portions of the flattened hose. The force transmission means transmits the force from the central portion of the flattened hose to the force sensor. Here, only deformations of the central portion caused by the internal pressure of the hose have an effect.

A corresponding force sensor 19 may also be arranged at the opposite end of the web 17 where a further foot corresponding to the foot 18 is provided.

The web 17 is a solid body, which, for example, consists of a rigid plate. The upper end 20 of the web 17 presses directly against the periphery of the hose 14 in the central portion of the hose flattened between the supporting bodies 10 and 11, where the hose wall extends linearly.

Figure 2:
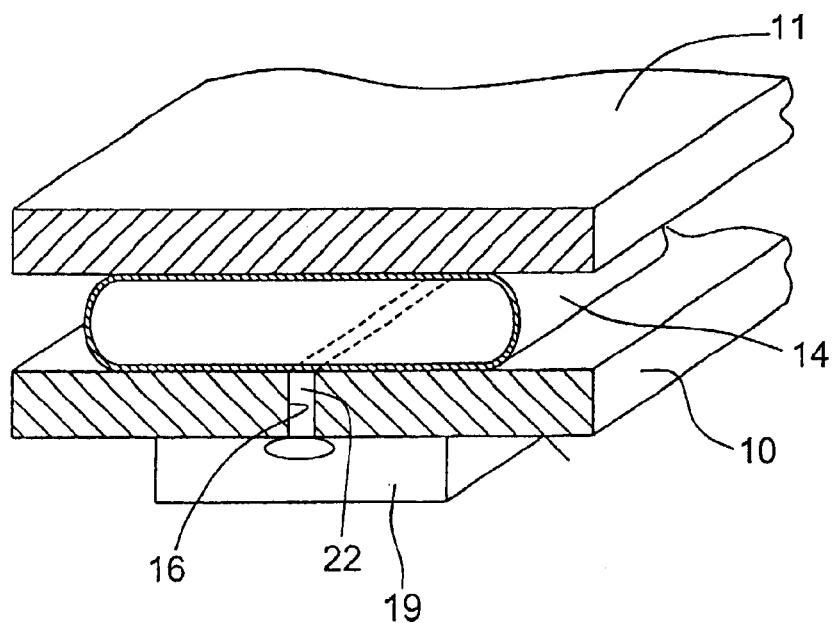
FIG. 2 shows, in the same manner as FIG. 1, a pressure sensor with an incompressible gel.

In the embodiment of FIG. 2, the one supporting body 10 is also provided with a longitudinally extending gap 16, and at the side of the supporting body 10 facing away from the hose 14, a force sensor 19 covering the gap 16 is mounted. The gap 16 is filled with a force transmission means consisting of an incompressible gel 22. At one end, this gel 22 presses against the straight portion of the wall of the flattened hose 14 and at the other end, it presses against the pressure-sensitive surface of the force sensor 19. The gel 22 may be confined by deformable membranes covering the gap 16 at the upper and under surfaces thereof. The gel 22 forms a force transmission means transmitting the deformation of the hose wall, which depends on the internal pressure, to the force sensor 19.

In both cases, only the hose deformation at the gap 16 is evaluated for generating the force signal when the pressure in the hose 14 changes. The force sensor 19 generates an electrical signal that is proportional to the internal pressure of the hose with high precision.

Since the deformation forces are received by the supporting bodies, the central portion of the hose rests on the force transmission means like a membrane. If pressure is generated in the hose, the pressure force proportional to the cross-sectional area of the gap is transferred to the force sensor via the force transmission means. From the cross-sectional area A of the force transmission means and the force F, the pressure P in the hose can be calculated as P=F×A. The force signal is evaluated in a microprocessor.

In the embodiment of the invention, a pressure of 1 bar corresponds to a force of 100,000 N/m5. With a surface area of the gap of 10 mm×2 mm, this results in 2 N/bar. In this case, the proportionality factor amounts to 0.5.

VARIATIONS AND EQUIVALENTS

It is understood that variations may be made in the foregoing without departing from the scope of the invention. For example, the force transmission means may be a web, a gel, a membrane or another form that transmits force relative to the support member. In an exemplary embodiment, the force transmission means may comprise a web extending in longitudinal direction of the hose. This web may be a solid web or may also comprise an incompressible gel. What is important is that the web is movable relative to the supporting body through which it extends and engages the flattened hose in its central portion so that it is largely freed from the forces generated by compressing the hose.

In an exemplary embodiment, the supporting bodies may have plane supporting surfaces, but it is also possible to provide a trough in the one supporting body and to provide the other supporting body with a level or slightly concave supporting surface.

In an exemplary embodiment, the force sensor may be a sensor with a particularly low excursion, the maximum excursion amounting to less than 1 mm. Thereby, the additional deformation caused by the internal pressure of the hose is kept small and the influence of the hose material upon the measuring result is limited.

For supporting the force transmission means, several force sensors may be provided which are arranged so as to be distributed in longitudinal direction of the hose.

Further, spacial references such as "top", "bottom", "upper", "under", and "central" are for purposes of illustration only, relative to the figures shown and are not limited to the specific orientation of the structure or movement directions as described.

Although only a few exemplary embodiments of this invention have been described in detail above, those skilled in the art will readily appreciate that many other modifications are possible in the exemplary embodiments without materially departing from the novel teachings and advantages of this invention. Accordingly, all such modifications are intended to be included within the scope of this invention as defined in the following claims.

What is claimed is:

1. A pressure sensor comprising a hose for passing a fluid, two supporting bodies deforming the cross-section of the hose, and a force sensor reacting to the internal pressure of the hose, characterized in that at least one of the supporting bodies includes a force transmission means which extends over less than 25% of the lumen of the hose deformed by the supporting bodies, which is movable relative to this supporting body and presses against the hose with one end and against the force sensor with the other end.

2. The pressure sensor according to claim 1, characterized in that the force sensor is mounted to the supporting body including the force transmission means.

3. The pressure sensor according to claims 1, characterized in that the force transmission means consists of an incompressible gel.

4. The pressure sensor according to claim 1, characterized in that the force transmission means is arranged in a gap extending through the supporting body.

5. The pressure sensor according to claim 4, characterized in that the gap extends in longitudinal direction of the hose and in the middle of the cross-section thereof.

6. The pressure sensor according to claim 1, characterized in that the force transmission means consists of an elongate web.

7. The pressure sensor according to claim 6, characterized in that the web is a solid web.

8. A pressure sensor comprising a hose for passing a fluid, two supporting bodies deforming the cross-section of the hose, and a force sensor reacting to the internal pressure of the hose, wherein at least one of the supporting bodies includes a force transmission means which extends over less than 25% of the lumen of the hose deformed by the supporting bodies, which force transmission means is movable relative to the at least one supporting body and presses against the hose with one end of the force transmission means and against the force sensor with another end of the force transmission means.

9. The pressure sensor according to claim 8, wherein the force sensor is mounted to the at least one supporting body including the force transmission means.

10. The pressure sensor according to claim 8 wherein the force transmission means comprises an incompressible gel.

11. The pressure sensor according to claim 8, wherein the force transmission means is arranged in a gap extending through the at least one supporting body.

12. The pressure sensor according to claim 8, wherein the gap extends in longitudinal direction of the hose and in the middle of the cross-section thereof.

13. The pressure sensor according to claim 8, wherein in the force transmission means comprises an elongate web.

14. The pressure sensor according to claim 13, wherein the web comprises a solid web.

* * * * *